United States Patent
Javet et al.

(10) Patent No.: US 6,740,128 B2
(45) Date of Patent: *May 25, 2004

(54) AGENT FOR COLORING FIBERS

(75) Inventors: Manuela Javet, Marly (CH); Catherine Mueller, Marly (CH)

(73) Assignee: Wella Aktiengesellschaft, Darmstadt (DE)

( * ) Notice: Subject to any disclaimer, the term of this patent is extended or adjusted under 35 U.S.C. 154(b) by 183 days.

This patent is subject to a terminal disclaimer.

(21) Appl. No.: 10/019,204
(22) PCT Filed: Mar. 9, 2001
(86) PCT No.: PCT/EP01/02684
§ 371 (c)(1), (2), (4) Date: Dec. 20, 2001
(87) PCT Pub. No.: WO01/85111
PCT Pub. Date: Nov. 15, 2001

(65) Prior Publication Data
US 2003/0101520 A1 Jun. 5, 2003

(30) Foreign Application Priority Data
May 10, 2000 (DE) .......................... 100 22 743

(51) Int. Cl.[7] .................................. A61K 7/13
(52) U.S. Cl. ...................... 8/405; 8/409; 8/424; 8/426; 8/565; 8/597; 8/608; 548/455; 548/511
(58) Field of Search ............................ 8/405, 409, 424, 8/426, 565, 597, 608; 548/455, 511

(56) References Cited
U.S. PATENT DOCUMENTS
4,542,224 A * 9/1985 Raue et al. .................. 548/455

FOREIGN PATENT DOCUMENTS

| | | |
|---|---|---|
| DE | 197 17 281 A1 | 10/1998 |
| DE | 299 08 464 U1 | 9/1999 |
| DE | 198 56 342 A | 6/2000 |
| FR | 2 787 707 A | 6/2000 |
| GB | 1 528 590 A | 10/1978 |
| GB | 0 847 749 A | 6/1998 |

* cited by examiner

*Primary Examiner*—Yogendra N. Gupta
*Assistant Examiner*—Eisa Elhilo
(74) *Attorney, Agent, or Firm*—Michael J. Striker

(57) ABSTRACT

The object of the invention is a preparation for dyeing fibers, especially hair, which is prepared before use by mixing an acidic component (A1), containing at least an enamine of formula (I) or its acid addition salt of Formula (Ia)

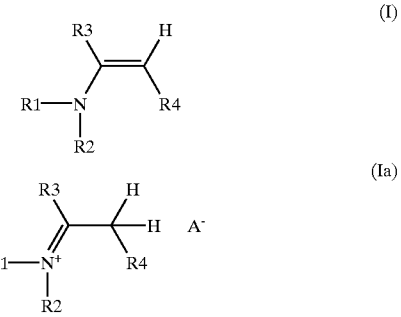

with an alkaline component (A2), containing at least one carbonyl compound and at least one primary amine, as well as a method for temporarily dyeing fibers, by means of which the coloration, obtained with the aforementioned dyeing preparation, is removed once again at any later time by a sulfite-containing decolorizing agent.

11 Claims, No Drawings

AGENT FOR COLORING FIBERS

The object of the present invention is a preparation for dyeing fibers, especially of human hair, it being also possible to decolorize the dyeing obtained gently once again at a later time, should this be desired.

Hair-coloring preparations are divided mainly into the areas of oxidation dyeing agents or of tints, depending on the original color of the hair, which is to be colored, and the desired end result. Oxidation hair dyes are outstandingly suitable for covering higher proportions of gray. The oxidation dyeing agents, which are used for gray portions up to 50%, usually are referred to as oxidative tints. On the other hand, the oxidation dyeing agents, which are used when the proportion of gray exceeds 50% or for "lightening" the color, usually are referred to as so-called oxidative dyes. Direct dyes are mainly contained in non-oxidative dyeing agents (so-called tinting agents). Because of their small size, some direct dyes, such as nitro dyes, can penetrate into the hair and dye it directly, at least in the outer regions. Such tints are very gentle to the hair and usually withstand 6 to 8 washings and enable up to about 20% gray to be covered.

In general, direct and oxidative tints are washed out when the hair is washed a few times. Among other factors, the period depends greatly on the structure of the hair and on the shade used. In some cases, oxidative dyes can fade over time. Usually, however, they remain in the hair until the next time the hair is cut. However, a hair coloring, which can be removed at any time, may be desirable for persons who wish to have a particular color only for a certain time or do not like the coloring achieved. Likewise, in the event that the hair is colored for the first time, the possibility of removing the coloring gently and completely reduces the fear of a too drastic change in color ("test coloring").

The German Offenlegungsschrift 197 17 281 discloses the use of a combination of benzylidene ketones and amines and/or hydroxy compounds and/or compounds containing acidic CH compounds for dyeing hair without the addition of oxidizing agents. Likewise the German utility patent 299 08 464 discloses that hair can be dyed permanently by a combination of certain 1,2,3,3-tetramethyl-3H-indolium salts and carbonyl compounds, even without the addition of oxidizing agents.

It is therefore an object of the present invention, to provide a dyeing preparation, which has a very long shelf life and makes possible, on the one hand, a gentle, intensive and stable coloring of the fibers without the use of an oxidizing agent, as well as a gentle and complete removal of this coloring at any time.

Surprisingly, it has now been found that this objective can be accomplished by using a preparation, which can be obtained by mixing a component, containing an enamine, with a component, which contains a carbonyl compound and a component, which contains a primary amine.

An object of the present invention therefore is a preparation for coloring fibers (A), such as wool, silk, cotton or hair and especially human hair, which is produced by mixing two components (A1) and (A2), wherein the component (A1) has an acidic pH and contains at least one enamine of Formula (I) or its acid addition salt of Formula (Ia)

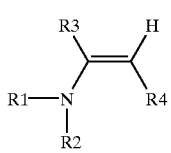
(I)

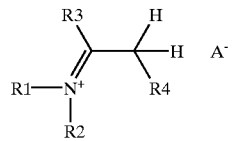
(Ia)

wherein R1 represents a single ring or multi-ring aromatic group, especially an unsubstituted 5-membered or 6-membered aryl group (preferably a phenyl group), an unsubstituted 5-membered or 6-membered heterocyclic group (preferably a pyridyl group or naphthyl group), a 5-membered or 6-membered aryl group, substituted with a C1 to C4 alkyl group, a C1 to C4 hydroxyalkyl group, a hydroxy group, a methoxy group, a dialkylamino group or a halogen group (F, Cl, Br, I) (preferably a substituted phenyl group), or a 5-membered or 6-membered heterocyclic group, substituted with a C1 to C4 alkyl group, a C1 to C4 hydroxyalkyl group, a hydroxy group, a methoxy group, a dialkylamino group or a halogen group (F, Cl, Br, I) (preferably a substituted pyridyl group or naphthyl group), R2 is a linear or branched C1 to C8 alkyl group, a linear or branched C1 to C8 hydroxyalkyl group or a C1 to C8 alkoxyalkyl group, wherein oxygen atoms may be located between the carbon atoms of the alkyl chain, R3 is a linear or branched C1 to C8 alkyl group, a C1 to C8 alkoxyalkyl group, a linear or branched C1 to C8 alkylene group, a C1 to C8 alkoxyalkylene group, an oxygen atom, a sulfur atom, an —NH group, or an —NR group, wherein R is an alkyl group, an alkoxyalkyl group, a hydroxyalkyl group or hydrogen, the R1 and R3 groups, together with the nitrogen atom and the carbon atom of the basic enamine structure being able to form a cyclic compound and R4 being hydrogen, a linear C1 to C4 alkyl group or a branched C1 to C4 alkyl group, A⁻ being the anion of an organic or inorganic acid, and the component (A2) having an alkaline pH and containing at least one carbonyl compound and at least one primary amine Preferred are compounds of Formula (I), in which the R1 and R3 groups together with the nitrogen atom and the carbon atom of the basic enamine structure form a cyclic compound, R3 preferably being linked to the aromatic R1 group at the carbon, which is in the ortho position to the enamine-substituted carbon.

Especially preferred are the following enamines of Formula (II) to (IX), in which X is a carbon atom, substituted with two C1 to C4 alkyl groups, which may be the same or different and, in particular, are two methyl groups, a carbon atom, substituted with a C1 to C4 alkyl group and a hydroxy group, a sulfur atom, an alkylated nitrogen atom, a not-alkylated nitrogen atom or an oxygen atom, and R2 is a linear or branched C1 to C8 alkyl group, a linear or branched C1 to C8 hydroxyalkyl group, or a C1 to C8 alkoxyalkyl group, in which there may be oxygen atoms between the carbon atoms of the alkyl chain, R4 is hydrogen, a linear C1 to C4 alkyl group or a branched C1 to C4 alkyl group, R5, R6, R7 and R8 independently of one another are hydrogen, a linear or branched C1 to C4 alkyl group, a linear or branched C1 to C4 hydroxyalkyl group, a hydroxy group, a methoxy group, an amino group, a monoalkylamino group, a dialkylamino group, a benzyl group or a halogen atom (F, Cl, Br, I) and A⁻ is chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenylborate, formate, acetate or propionate, the chloride ion, the tetrafluoroborate ion, the acetate ion and the hydrogen sulfate ion being particularly preferred.

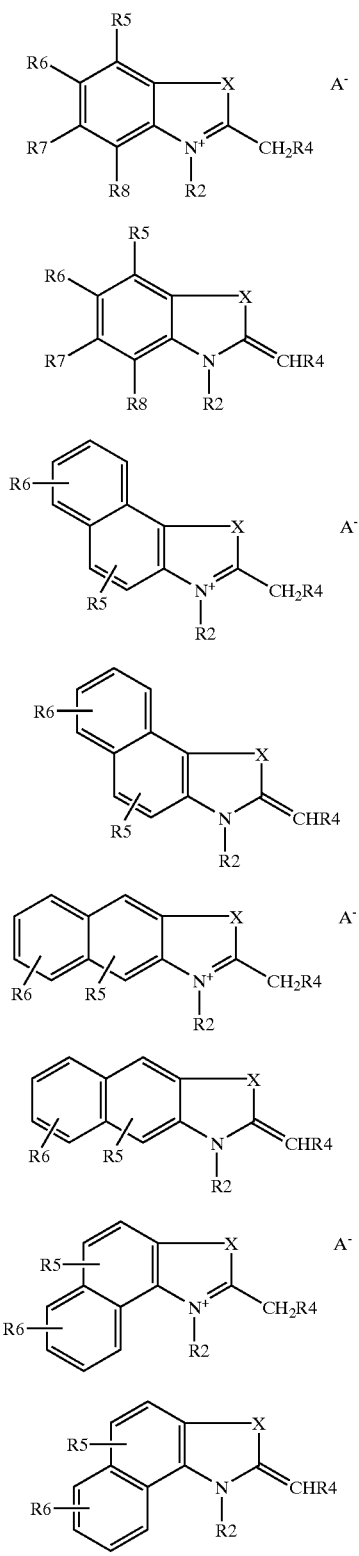

Of the compounds of the Formulas (II) to (IX), especially the following should be mentioned: 1,3,3-trimethyl-2-methylene-indoline as well as its salts, 1,3,3,4-tetramethyl-2-methylene-indoline as well as its salts, 1,3,3,5-tetramethyl-2-methylene-indoline as well as its salts, 1,3,3,6-tetramethyl-2-methylene-indoline as well as its salts, 1,3,3,7-tetramethyl-2-methylene-indoline as well as its salts, 1,3,3,6,7-pentamethyl-2-methylene-indoline as well as its salts, 1,3,3,5,7-pentamethyl-2-methylene-indoline as well as its salts, 1,3,3,4,7-pentamethyl-2-methylene-indoline as well as its salts, 5-chloro-1,3,3-trimethyl-2-methylene-indoline as well as its salts, 5-fluoro-1,3,3-trimethyl-2-methylene-indoline as well as its salts, 5-isopropyl-1,3,3-trimethyl-2-methylene-indoline as well as its salts, 5-hydroxy-1,3,3-trimethyl-2-methylene-indoline as well as its salts, 5-methoxy-1,3,3-trimethyl-2-methylene-indoline as well as its salts, 5-amino-1,3,3-trimethyl-2-methylene-indoline as well as its salts, 6-hydroxy-1,3,3-trimethyl-2-methylene-indoline as well as its salts, 6-methoxy-1,3,3-trimethyl-2-methylene-indoline as well as its salts, 5-methoxy-6-amino-1,3,3-trimethyl-2-methylene-indoline as well as its salts, 5,6-dihydroxy-1,3,3-trimethyl-2-methylene-indoline as well as its salts, 5,6-dimethoxy-1,3,3-trimethyl-2-methylene-indoline as well as its salts, 4,5-dihydroxy-1,3,3-trimethyl-2-methylene-indoline as well as its salts, 5,7-dihydroxy-1,3,3-trimethyl-2-methylene-indoline as well as its salts, 5-amino-6-methoxy-1,3,3-trimethyl-2-methylene-indoline as well as its salts, 5-amino-7-hydroxy-1,3,3-trimethyl-2-methylene-indoline as well as its salts, 5-hydroxy-7-amino-1,3,3-trimethyl-2-methylene-indoline as well as its salts, 1-(2'-hydroxyethyl)-3,3-dimethyl-2-methylene-indoline as well as its salts, 1,3,3-trimethyl-2-methylene-3H-benz[e]indole as well as its salts and N-ethyl-2-methylene-benzthiazole as well as its salts, of which 1,3,3-trimethyl-2-methylene-indoline, 1,2,3,3-tetramethyl-3H-indolium chloride, 1,2,3,3-tetramethyl-3H-indolium bromide, 1,2,3,3-tetramethyl-3H-indolium iodide, 1,2,3,3-tetramethyl-3H-indolium sulfate, 1,2,3,3-tetramethyl-3H-indolium-hydrogen sulfate, 1,2,3,3-tetramethyl-3H-indolium-methyl sulfate, 1,2,3,3-tetramethyl-3H-indolium-hexafluorophosphate, 1,2,3,3-tetramethyl-3H-indolium-hexafluoroantimonate, 1,2,3,3-tetramethyl-3H-indolium-tetrafluoroborate, 1,2,3,3,5-pentamethyl-3H-indolium iodide, 1,2,3,3,7-pentamethyl-3H-indolium-tetrafluoroborate, 1,2,3,3,6,7-hexamethyl-3H-indolium-tetrafluoroborate, 1,2,3,3,5,7-hexamethyl-3H-indolium-tetrafluoroborate, 1,2,3,3,4,7-hexamethyl-3H-indolium-tetrafluoroborate, 5-chloro-1,2,3,3-tetramethyl-3H-indolium iodide, 5-fluoro-1,2,3,3-tetramethyl-3H-indolium iodide, 5-isopropyl-1,2,3,3-tetramethyl-3H-indolium iodide, 5-methoxy-1,2,3,3-tetramethyl-3H-indolium iodide, 5-hydroxy-1,2,3,3-tetramethyl-3H-indolium iodide, 1,2,3,3-tetramethyl-3H-benz[e]indolium chloride, 1,2,3,3-tetramethyl-3H-benz[e]indolium bromide, 1,2,3,3-tetramethyl-3H-benz[e]indolium iodide, 1,2,3,3-tetramethyl-3H-benz[e]indolium sulfate, 1,2,3,3-tetramethyl-3H-benz[e]indolium-hexafluorophosphate, 1,2,3,3-tetramethyl-3H-benz[e]indolium-methyl sulfate, 1,2,3,3-tetramethyl-3H-benz[e]indolium-hexafluoroantimonate, 1,2,3,3-tetramethyl-3H-benz[e]indolium-tetrafluoroborate, 1,2-dimethyl-benzthiazolium iodide and N-ethyl-2-methylbenzthiazolium iodide are especially preferred.

As carbonyl compounds, suitable for use in component (A2), the following aldehydes, in particular, are named: 4-hydroxy-3-methoxybenzaldehyde (vanillin), 3-hydroxy-4-methoxybenzaldehyde (isovanillin), 3,4-dihydroxy-benzaldehyde, 4-hydroxybenzaldehyde, 3,5-dimethoxy-4-hydroxybenzaldehyde, 4-dimethylamino-benzaldehyde, 4-methyl-5-imidazole-carboxaldehyde, 4-dimethylamino-cinnamaldehyde, 4-hydroxy-2-methoxybenzaldehyde, 3,5-dimethyl-4-hydroxybenzaldehyde, 4-dimethylamino-2- methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxybiphenyl-1-carbaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxy-benzaldehyde, 3,4,5-trihydroxybenzaldehyde, 2,4,6-trihydroxbenzaldehyde, 2,4-dimethoxybenzaldehyde, 2,3-dimethoxybenzaldehyde, 2,5-dimethoxy-benzaldehyde, 3,5-dimethoxybenzaldehyde, 3,4-dimethoxybenzaldehyde, indole-3-carbaldehyde, benzene-1,4-dicarbaldehyde, 4-ethoxybenzaldehyde, 2-methyl-1,4-napthoquinone, 4-carboxybenzaldehyde, 4-hydroxy-3-methoxy-cinnamaldehyde, 3,5-dimethoxy-4-hydroxycinnamaldehyde, 3-methoxy-4-(1-pyrrolidinyl) benzaldehyde, 4-diethylamino-3-methoxybenzaldehyde, 1,2-phthaldialdehyde, pyrrole-2-aldehyde, thiophene-2-aldehyde, thiophene-3-aldehyde, chromone-3-carboxaldehyde, 6-methyl-4-oxo-1(4H)-benzopyran-3-carbaldehyde, N-methylpyrrole-2-aldehyde, 5-methylfurfural, 6-hydroxy-chormen-3-carboxaldehyde, 6-methylinodole-3-carboxaldehyde, 4-dibutylamino-benzaldehyde, N-ethylcarbazole-3-aldehyde, 4-diethylamino-2-hydroxy-benzaldehyde, 3,4-dimethoxy-5-hydroxybenzaldehyde, 5-(4-(diethylamino)-phenyl)-2,4-pentadienal, 2,3-thiophenedicarboxaldehyde, 2,5-thiophene-dicarboxaldehyde, 2-methoxy-1-naphthaldehyde, 3-ethoxy-4-hydroxy-benzaldehyde, 2-nitrobenzaldehyde, 3-nitrobenzaldehyde and 4-nitrobenzaldehyde.

As primary amines, suitable for use in component (A2), the following compounds, in particular, are named: alkanolamine, such as monoethanolamine, 1-amino-2-propanol or 3-amino-1-propanol, or aromatic amines, such as 1,4-diaminobenzene, 1,4-diamino-2-methylbenzene, 1,4-diamino-2,6-dimethyl-benzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)-amino]-aniline, 4-[(2-methoxyethyl)-amino]-aniline, 4-[(3-hydroxypropyl)-amino]-aniline, 1,4-diamino-2-(2-hydroxy-ethyl)-benzene, 1,4-diamino-2-(1-methylethyl)benzene, 1,3-bis[(4-amino-phenyl)(2-hydroxyethyl)amino]-2-propanol, 1,8-bis(2,5-diaminophenoxy)-3,6-dioxaoctane, 4-aminophenol, 4-amino-3-methyl-phenol, 4-methylamino-phenol, 4-amino-2-(amino-methyl)phenol, 4-amino-2-[(2-hydroxyethyl)amino]-methylphenyl, 4-amino-2-(methoxymethyl)phenol, 4-amino-2-(2-hydroxyethyl)-phenol, 5-aminosalicylic acid, 2,5-diamino-pyridine, 2,4,5,6-tetraaminopyrimidine, 2,5,6-triamino-4-(1H)-pyrimidone 4,5-diamino-1-(2-hydroxyethyl)-1H-pyrazole, 4,5-diamino-1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, 2,6-diamino-pyridine, 2-amino-4-[(2-hydroxyethyl)-amino]anisole, 2,4-diamino-1-fluoro-methylbenzene, 2,4-diamino-1-methoxy-5-methylbenzene, 2,4-diamino-1-methoxy-5-methylbenzene, 2,4-diamino-1-(2hydroxyethoxy)-5-methyl-benzene, 2,3-diamino-6-methoxypridine, 3-amino-6-methoxy-2-(methylamino) pyridine, 2,6-diamino-3,5-dimethosypyridine, 3,5-diamino-2,6-dimethoxy-pyridine, 1,3-diaminobenzene, 2,4diamino-1-(2-hydroxyethoxy)-benzene, 1-(2-aminoethoxy)-2,4-diamino-benzene, 2-amino-1-(2-hydroxyethoxy)-4-methylaminobenzene, 2,4-diaminophenoxy-acetic acid, 3-[di(2-hydroxyethyl)amino]-aniline, 4-amino-2-di[(2-hydroxyethyl)-amino]-1-ethoxybenzene, 3-[(2-hydroxyethyl)amino]-aniline, 3-[(2-amino-ethyl)amino] aniline, 1,3-diamino-2,4-dimethoxybenzene, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichloro-phenol, 3-amino-2-methylphenol, 3-amino-2-chloro-6-methylphenol, 3-aminophenol, 5-amino-2-ethylphenol,2-amino-3-hydroxypyridine, 5-amino-4-chloro-2-methylphenol, 3,4-diaminobenzoic acid, 6-amino-3,4-dihydro-1,4(2H)-benzoxazine or their salts, or amino acids, such as arginine, lysine, tyrosine, histidine, phenylalanine or tryptophan.

The enamines of formulas (I) to (IX), the carbonyl compounds and the primary amines are contained in the ready-for-use component (A) in each case in a total amount of about 0.01 to 10% by weight and preferably of about 0.1 to 5% by weight.

The form, in which the components (A1) and (A2) and the ready-for-use dyeing agent (A) are prepared maybe, for example a solution, especially an aqueous or aqueous-alcoholic solution, a cream, a gel or an emulsion. Its composition represents a mixture of the enamines of formula (I) and of the carbonyl compounds and amines with the additives, which are customary for such preparations.

Customary additives, used in dyeing agents in solutions, creams, emulsions, gels or aerosol foams are, for example, solvents such as water, low molecular weight aliphatic alcohols, such as ethanol, n-propanol and isopropanol, or glycols, such as glycerin and 1,2-dihydroxypropane, wetting agents or emulsifiers, from the classes of anionic, cationic, amphoteric or nonionic surface-active substances, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters, thickeners, such as high molecular weight fatty alcohols, starch or cellulose derivatives, perfumes, hair pre-treatment materials, conditioners, hair-swelling agents, preservatives, Vaseline, paraffin oil and fatty acids, as well as care materials, such as cationic resins, lanolin derivatives, cholesterol, pantothenic acid and betaine. The components mentioned are used in amounts customary for such purposes; for example, the wetting agents and emulsifiers are used in concentrations of about 0.5 to 30% by weight, the thickeners in an amount of about 0.1 to 25% by weight and the care materials in a concentration of about 0.1 to 5.0% by weight.

Furthermore, the inventive dyeing agent optionally may contain additional, conventional, physiologically safe direct dyes from the group of nitro dyes, azo dyes, quinone dyes and triphenylmethane dyes. These direct dyes may be used in component (A1) and/or component (A2) in each case in a total amount of about 0.02 to 20% by weight and preferably of 0.2 to 10% by weight, the total amount of direct dyes in the ready-for-use dyeing agent, obtained by mixing components (A1) and (A2), being about 0. 01 to 10% by weight and preferably 0.1 to 5% by weight.

The pH of the ready-for-use dyeing agent (A) usually is 3 to 12 and preferably about 6 to 11, the pH of the ready-for-use dyeing agent (A) during the mixing of the acidic component (A1) and the alkaline component (A2) reaching a value, which is affected by the amount of acid in component (A1) and the amount of alkali in component (A2), as well as by the ratio, in which these two components are mixed.

Component (A1) preferably has a pH of about 1 to 4.5 and especially of 1.5 to 3, while component (A2) preferably has a pH of 7.5 to 12 and especially 8 to 11.

For adjusting the pH of components (A1) and (A2) and of the ready-for-use dyeing agent (A) to the value desired for the coloring, alkalizing agents, such as alkanolamines, alkylamines, alkali hydroxides or ammonium hydroxide and alkali carbonates or ammonium carbonates, or acids, such as lactic acid, acetic acid, tartaric acid, phosphoric acid, hydrochloric acid, citric acid, ascorbic acid or boric acid may, if necessary, be used.

The ready-for-use dyeing agent is prepared immediately before use by mixing components (A1) and (A2) and then applied on the fibers, especially on human hair. This mixture is allowed to act for 5 to 60 minutes and preferably for 15 to 30 minutes at a temperature of about 20° C. to 50° C. and especially at 30° C. to 40° C., depending on the depth of color desired. Subsequently, the fibers are rinsed with water and optionally washed with a shampoo.

A further object of the present invention is a multi-component kit, consisting of a preparation of component (A1), a preparation of component (A2), as well as, optionally, a preparation for adjusting the pH. Of course, the preparations of components (A1) and (A2) may also consist of several individual components, which are mixed together only immediately before use. However, a two-component kit, consisting of a preparation of component (A1) and a preparation of component (A2), is particularly preferred.

The inventive dyeing agent has a long shelf life and enables the fibers, especially keratin fibers such as human hair, to be colored gently, uniformly and durably, the coloration obtained not becoming darker afterwards. Surprisingly, these colorations can be removed again in a simple and gentle manner at any time by sulfites.

A further object of the present invention therefore is a method for temporarily coloring fibers, for which the fibers initially are colored with the inventive dyeing agent (A) and the coloration is removed once again at any later time with a decolorizing agent, which contains at least one sulfite, as well as a multi-component kit for dyeing and later decolorizing fibers, containing the inventive dyeing agent (A) as well as a sulfite-containing decolorizing agent (B).

As sulfite, ammonium sulfite, alkali sulfites or alkaline earth sulfites, for example, can be used, sodium sulfite and ammonium sulfite being particularly preferred. The total amount of sulfite in the decolorizing agent is about 0.1 to 10% by weight and preferably 2 to 5% by weight.

This decolorizing agent can be in the form of an aqueous or an aqueous alcoholic solution, a gel, a cream, an emulsion or a foam. Moreover, the decolorizing agent can be in the form of a one-component preparation as well as in the form of a multi-component preparation. Aside from being in powder form, the decolorizing agent may also be in the form of a tablet, such as an effervescent tablet, or a granulate, as protection against the formation of dust. Before use, the decolorizing agent is prepared from this with cold or warm water, optionally with the addition of one or more of the adjuvants named below. It is, however, also possible that these adjuvants, if they are in solid form, are already contained in the decolorizing powder or decolorizing granulates or the effervescent tablet. Dust formation can be reduced additionally by wetting the powder with oils or waxes.

The dyeing agent may contain additional adjuvants, for example, solvents such as water, low molecular weight alcohols, such as ethanol, n-propanol and isopropanol, glycol ethers or glycols, such as glycerin and, in particular 1,2-dihydroxy propane, wetting agents or emulsifiers from the classes of anionic, cationic, amphoteric or nonionic surface-active substances, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty alcohols, ethoxylated nonylphenol, fatty acid alkanolamides, ethoxylated fatty acid esters, thickeners such as high molecular weight fatty alcohols, starch or cellulose derivates, perfumes, hair-pre-treatment preparations, conditioners, hair swelling agents, preservatives, Vaseline, paraffin oil and fatty acids, as well as care materials, such as cationic resins, lanolin derivatives, cholesterol, pantothenic acid and betaine.

The pH of the decolorizing agent is about 3 to 8 and especially 4 to 7. If necessary, the desired pH can be obtained by adding suitable acids, for example, α-hydroxycarboxylic acids, such as lactic acid, tartaric acid, citric acid or malic acid, phosphoric acid, acetic acid, glycolic acid, salicylic acid, glutathione or gluconic acid lactone, or alkalizing agents such as alkanolamines, alkylamines, alkali hydroxides, ammonium hydroxide, alkali carbonates, ammonium carbonates or alkali phosphates.

For decolorizing fibers colored with the inventive preparation, the decolorizing agent is applied on the fibers and allowed to act at about 20° C. to 50° C. for a period of 5 to 60 minutes and especially 15 to 30 minutes. At the end of the period of action of the decolorizing agent, the hair is rinsed with water, optionally washed with a shampoo and subsequently dried.

The following examples are intended to explain the object in greater detail without limiting it to the examples.

EXAMPLES

Examples 1.1 to 1.35: Hair Coloring Preparation

| Component (A1) | |
|---|---|
| Compound of Formula (I) | according to Table 1 |
| 6-O-palmitoyl-L-ascorbic acid | 0.3 g |
| cetyl stearyl alcohol | 12.0 g |
| lauryl ether sulfate, 28% aqueous solution | 10.0 g |
| ethanol | 23.0 g |
| water, fully desalinated | ad 100.0 g |

The cetyl stearyl alcohol is melted at 80° C. The lauryl ether sulfate and 95% of the water are heated to 80° C. and added to the molten cetyl stearyl alcohol and stirred until a cream results. The compound of Formula (I), the ethanol and the remaining water and the 6-O-palmitoyl-L-ascorbic acid are added at room temperature.

| Component (A2) | |
|---|---|
| aldehyde compound | according to Table 1 |
| primary amine | according to Table 1 |
| cetyl stearyl alcohol | 12.0 g |
| lauryl ether sulfate, 28% aqueous solution | 10.0 g |
| ethanol | 23.0 g |
| water, fully desalinated | ad 100.0 g |

The cetyl stearyl alcohol is melted at 80° C. The lauryl ether sulfate and 95% of the water are heated to 80° C. and added to the molten cetyl stearyl alcohol and stirred until a cream results. The aldehyde, the ethanol and the remaining water are added at room temperature. The pH of the cream is adjusted with the respective primary amine, optionally with addition of 10% sodium hydroxide solution, to the value given in Table 1.

Component (A1) and Component (A2) are mixed in a ratio of 1:1. The ready-for-use hair coloring preparation, so obtained, is applied on the hair and distributed uniformly with a brush. After a period of action of 30 minutes at 40° C., the hair is washed with a shampoo, subsequently rinsed with lukewarm water and then dried.

The hair can be decolorized once again completely at any time, for example, after several days or weeks, with a 5% sodium sulfite solution (pH=5) within a period of 20 minutes at 40° C. The coloring and decolorizing results are given in the following Table 1.

The L*a*b* measured color values are determined with a Minolta Chromameter II colorimeter. The L value represents the luminosity (this means that L value varies inversely with the color intensity), while the a value is a measure of the red portion (that is, the a value varies with the red portion) and the b value is a measure of the blue portion of the color, a more negative b value indicating a greater proportion of blue.

Unless stated otherwise, the percentages in the present application are percentages by weight.

TABLE 1

| No. | Compound (I) contained in Component (A1); Aldehyde/Amine Combination contained in Component (A2) | Shade after the coloring | | Measured Color Values | | | Shade after the decolorizing |
|---|---|---|---|---|---|---|---|
| | | | | L | a | b | |
| 1.1 | (A1) 1,2,3,3-tetramethyl-3H-indolium hydrogen sulfate: 3.13 g; (A2) 4-hydroxy-3-methoxy-benzaldehyde: 1.76 g and monoethanolamine to pH 9.6 | intensive red | Untreated hair: After the coloring: | +83.30; +27.42 | −0.48; +58.13; | +10.40 +13.45 | white |
| 1.2 | (A1) 1,2,3,3-tetramethyl-3H-indolium chloride: 2.42 g; (A2) 4-hydroxybenzaldehyde: 1.43 g and monoethanolamine to pH 9.6 | intensive orange | Untreated hair: After the coloring: | +83.30; +45.09 | −0.48; +72.03; | +10.40 +45.34 | white |
| 1.3 | (A1) 1,2,3,3-tetramethyl-3H-indolium chloride: 2.42 g; (A2) 3-hydroxy-4-methoxy-benzaldehyde: 1.76 g and monoethanolamine to pH 9.6 | intensive yellow | Untreated hair: After the coloring: | +83.30; +57.17 | −0.48; +37.79; | +10.40 +65.95 | white |
| 1.4 | (A1) 1,2,3,3-tetramethyl-3H-indolium hydrogen sulfate: 3.13 g; (A2) 3,5-dimethoxy-4-hydroxy-benzaldehyde: 2.10 g and monoethanolamine to pH 9.5 | intensive violet | Untreated hair: After the coloring: | +83.30; +21.74 | −0.48; +45.39; | +10.40 +0.74 | white |
| 1.5 | (A1) 1,2,3,3-tetramethyl-3H-indolium hydrogen sulfate: 3.13 g; (A2) 3,4-dihydroxybenzaldehyde: 1.59 g and monoethanolamine to pH 9.5 | intensive wine red | Untreated hair: After the coloring: | +83.30; +21.27 | −0.48; +29.77; | +10.40 +4.68 | white |
| 1.6 | (A1) 1,2,3,3-tetramethyl-3H-indolium hydrogen sulfate: 3.13 g; (A2) 4-dimethylaminobenzaldehyde: 1.72 g and monoethanolamine pH 10.8 | intensive pink | Untreated hair: After the coloring: | +83.30; +37.10 | −0.48; +77.63; | +10.40 +4.80 | pale pink |
| 1.7 | (A1) 1,2,3,3-tetramethyl-3H-indolium hydrogen sulfate: 3.13 g; (A2) 4-dimethylamino-cinnamaldehyde: 2.02 g and monoethanolamine to pH 11.1 | green | Untreated hair: After the coloring: | +83.30; +23.71 | −0.48; −0.91; | +10.40 +10.19 | |
| 1.8 | (A1) 1,2,3,3-tetramethyl-3H-indolium hydrogen sulfate: 3.13 g; (A2) 4-carboxybenzaldehyde: 1.73 g and monoethanolamine to pH 9.6 | yellow | Untreated hair: After the coloring: | +83.30; +77.75 | −0.48; +5.18; | +10.40 +62.84 | white |
| 1.9 | (A1) 1,2,3,3-tetramethyl-3H-indolium hydrogen sulfate: 3.13 g; (A2) 4-hydroxy-3-methoxy-cinnamonaldehyde: 2.06 g and monoethanolamine to pH 9.6 | reddish brown | Untreated hair: After the coloring: | +83.30; +20.24 | −0.48; +9.22; | +10.40 +3.82 | |
| 1.10 | (A1) 1,2,3,3-tetramethyl-3H-indolium hydrogen sulfate: 3.13 g; (A2) 2,3,4-trihydroxybenzaldehyde: 1.78 g and monoethanolamine to pH 9.76 | rust red | Untreated hair: After the coloring: | +83.30; +30.92 | −0.48; +42.44; | +10.40 +16.79 | white |
| 1.11 | (A1) 1,2,3,3-tetramethyl-3H-indolium hydrogen sulfate: 3.13 g; (A2) 3,4,5-trihydroxybenzaldehyde: 1.78 g and monoethanolamine to pH 9.6 | dark violet | Untreated hair: After the coloring: | +83.30; +18.83 | −0.48; +16.73; | +10.40 +0.33 | white |

TABLE 1-continued

| No. | Compound (I) contained in Component (A1); Aldehyde/Amine Combination contained in Component (A2) | Shade after the coloring | | Measured Color Values | | | Shade after the decolorizing |
|---|---|---|---|---|---|---|---|
| | | | | L | a | b | |
| 1.12 | (A1) 1,2,3,3-tetramethyl-3H-indolium hydrogen sulfate: 3.13 g; (A2) 4-methylimidazo-5-carboxaldehyde: 1.27 g and monoethanolamine to pH 10.7 | intensive yellow | Untreated hair: After the coloring: | +83.30; +75.19 | −0.48; +11.17; | +10.40 +95.17 | white |
| 1.13 | (A1) 1,2,3,3-tetramethyl-3H-indolium hydrogen sulfate: 3.13 g; (A2) 4-dimethylamino-2-methoxy-benzaldehyde: 1.72 g and monoethanolamine to pH 10.8 | pink | Untreated hair: After the coloring: | +83.30; +1.13 | −0.48; +1.55; | +10.40 +3.05 | white |
| 1.14 | (A1) 1,2,3,3-tetramethyl-3H-indolium hydrogen sulfate: 3.13 g; (A2) 4-hydroxy-2-methoxy-benzaldehyde: 1.75 g and monoethanolamine to pH 10.1 | intensive orange | Untreated hair: After the coloring: | +83.30; +39.14 | −0.48; +66.62; | +10.40 +35.19 | white |
| 1.15 | (A1) 1,2,3,3-tetramethyl-3H-indolium hydrogen sulfate: 3.13 g; (A2) 3,5-dimethyl-4-hydroxy-benzaldehyde: 1.73 g and monoethanolamine to pH 9.6 | intensive orange-red | Untreated hair: After the coloring: | +83.30; +34.02 | −0.48; +68.43; | +10.40 +24.74 | white |
| 1.16 | (A1) 1,2,3,3-tetramethyl-3H-indolium hydrogen sulfate: 3.13 g; (A2) 4-hydroxy-3-methoxy-benzaldehyde: 1.76 g and monoethanolamine to pH 9.6 | intensive red | Untreated hair: After the coloring: | +83.30; +28.20 | −0.48; +61.81; | +10.40 +15.57 | white |
| 1.17 | (A1) 1,2,3,3-tetramethyl-3H-indolium hydrogen sulfate: 3.13 g; (A2) 4-hydroxy-3-methoxy-benzaldehyde: 1.76 g and 3-amino-1-propanol to pH 9.6 | intensive red | Untreated hair: After the coloring: | +83.30; +29.29 | −0.48; +62.30; | +10.40 +16.76 | |
| 1.18 | (A1) 3-ethyl-2-methyl-benzothiazolium-iodide: 3.52 g; (A2) 4-hydroxy-3-methoxy-benzaldehyde: 1.76 g and monoethanolamine to pH 9.3 | intensive red | Untreated hair: After the coloring: | +83.30; +26.20 | −0.48; +53.73; | +10.40 +14.67 | |
| 1.19 | (A1) 3-ethyl-2-methyl-benzothiazolium iodide: 3.52 g; (A2) 3-hydroxy-4-methoxy-benzaldehyde: 1.76 g and monoethanolamine to pH 9.0 | intensive yellow | Untreated hair: After the coloring: | +83.30; +61.32 | −0.48; +23.05; | +10.40 +66.21 | |
| 1.20 | (A1) 1,2,3,3-tetramethyl-3H-indolium-hydrogen sulfate: 3.13 g; (A2) 3-hydroxy-4-methoxy-benzaldehyde: 1.76 g and 1,4-diamino-2-methylbenzene: 2.80 g and NaOH (10%) to pH 10 | dark red | Untreated hair: After the coloring: | +83.30; +25.54 | −0.48; +50.26; | +10.40 +11.63 | |
| 1.21 | (A1) 1,2,3,3-tetramethyl-3H-indolium hydrogen sulfate: 3.13 g; (A2) 3-hydroxy-4-methoxy-benzaldehyde: 1.76 g and 4-amino-3-methylphenol: 1.75 g and NaOH (10%) to pH 10 | intensive red | Untreated hair: After the coloring: | +83.30; +24.76 | −0.48; +49.52; | +10.40 +11.57 | |
| 1.22 | (A1) 1,2,3,3-tetramethyl-3H-indolium hydrogen sulfate: 3.13 g; (A2) 3-hydroxy-4-methoxy-benzaldehyde: 1.76 g and 1,4-diamino-2(2-hydroxyethyl)-benzene: 3.2 g and NaOH (10%) to pH 10 | dark red | Untreated hair: After the coloring: | +83.30; +25.54 | −0.48; +48.80; | +10.40 +12.10 | |
| 1.23 | (A1) 3-ethyl-2-methyl-benzothiazolium iodide: 3.52 g; (A2) 3-hydroxy-4-methoxy-benzaldehyde: 1.76 g and 2-amino-5-methylphenol: 1.6 g and NaOH (10%) to pH 10 | intensive red | Untreated hair: After the coloring: | +83.30; +24.31 | −0.48; +50.43; | +10.40 +10.58 | |

TABLE 1-continued

| No. | Compound (I) contained in Component (A1); Aldehyde/Amine Combination contained in Component (A2) | Shade after the coloring | | Measured Color Values L | a | b | Shade after the decolorizing |
|---|---|---|---|---|---|---|---|
| 1.24 | (A1) 1,2,3,3-tetramethyl-3H-indolium-hydrogensulfate: 3.13 g; | | Untreated hair: | +83.30; | −0.48; | +10.40 | |
| | (A2) 3-hydroxy-4-methoxy-benzaldehyde: 1.76 g and L-arginine to pH 9.2 | intensive red | After the coloring: | +28.29 | +61.89; | +14.20 | |
| 1.25 | (A1) 3-ethyl-2-methyl-benzothiazolium iodide: 3.52 g; | | Untreated hair: | +83.30; | −0.48; | +10.40 | |
| | (A2) 3-hydroxy-4-methoxy-benzaldehyde: 1.76 g and L-lysine 1.86 g and NaOH (10%) to pH 10 | intensive red | After the coloring: | +27.40 | +58.53; | +13.81 | |
| 1.26 | (A1) 1,2,3,3-tetramethyl-3H-indolium hydrogen sulfate: 3.13 g; | | Untreated hair: | +83.30; | −0.48; | +10.40 | |
| | (A2) 3-hydroxy-4-methoxy-benzaldehyde: 1.76 g and L-arginine 2.21 g and NaOH (10%) to pH 10 | intensive red | After the coloring: | +26.39 | +59.19; | +14.41 | |
| 1.27 | (A1) 3-ethyl-2-methyl-benzothiazolium iodide: 3.52 g; | | Untreated hair: | +83.30; | −0.48; | +10.40 | |
| | (A2) 3-hydroxy-4-methoxy-benzaldehyde: 1.76 g and L-histidine 1.97 g and NaOH (10%) to pH 9.5 | intensive red | After the coloring: | +26.41 | +55.93; | +11.78 | |
| 1.28 | (A1) 1,2,3,3-tetramethyl-3H-indolium hydrogen sulfate: 3.13 g; | | Untreated hair: | +83.30; | −0.48; | +10.40 | |
| | (A2) 3-hydroxy-4-methoxy-benzaldehyde: 1.76 g and L-tyrosine 2.30 g and NaOH (10%) to pH 10.5 | intensive red | After the coloring: | +28.11 | +62.16; | +14.81 | |
| 1.29 | (A1) 1,1,2,3-tetramethyl-1H-benz[e]indolium iodide: 4.08 g; | | Untreated hair: | +83.30; | −0.48; | +10.40 | |
| | (A2) 3-hydroxy-4-methoxy-benzaldehyde: 1.76 g and monoethanolamine to pH 9.6 | intensive yellow | After the coloring: | +49.28 | +44.23; | +51.99 | white |
| 1.30 | (A1) 1,1,2,3-tetramethyl-1H-benz[e]indolium iodide: 3.01 g; | | Untreated hair: | +83.30; | −0.48; | +10.40 | |
| | (A2) 4-hydroxybenzaldehyde: 1.43 g and monoethanolamine to pH 9.6 | intensive orange | After the coloring: | +33.59 | +65.37; | +25.68 | white |
| 1.31 | (A1) 1,1,2,3-tetramethyl-1H-benz[e]indolium iodide: 4.08 g; | | Untreated hair: | +83.30; | −0.48; | +10.40 | |
| | (A2) 4-hydroxy-3-methoxy-benzaldehyde; 1.76 g and monoethanolamine to pH 9.6 | intensive dark red | After the coloring: | +22.45 | +47.33; | +4.37 | white |
| 1.32 | (A1) 1,1,2,3-tetramethyl-1H-benz[e]indolium iodide: 3.01 g; | | Untreated hair: | +83.30; | −0.48; | +10.40 | |
| | (A2) 3,4-dihydroxybenzaldehyde: 1.60 g and monoethanolamine to pH 9.6 | intensive red violet | After the coloring: | +19.91 | +19.53; | −3.91 | white |
| 1.33 | (A1) 1,1,2,3-tetramethyl-1H-benz[e]indolium iodide: 4.08 g; | | Untreated hair: | +83.30; | −0.48; | +10.40 | |
| | (A2) 3,5-dimethoxy-4-hydroxy-benzaldehyde: 2.10 g and monoethanolamine to pH 9.6 | intensive blue-violet | After the coloring: | +19.29 | +25.78; | −8.10 | white |
| 1.34 | (A1) 1,1,2,3-tetramethyl-1H-benz[e]indolium iodide: 4.08 g; | | Untreated hair: | +83.30; | −0.48; | +10.40 | |
| | (A2) 3,4,5-trihydroxybenzaldehyde: 1.98 g and monoethanolamine to pH 9.5 | intensive blue | After the coloring: | +19.76 | +7.10; | −7.34 | white |
| 1.35 | (A1) 1,1,2,3-tetramethyl-1H-benz[e]indolium iodide: 4.08 g; | | Untreated hair: | +83.30; | −0.48; | +10.40 | |
| | (A2) 4-dimethylaminobenzaldehyde: 1.72 g and monoethanolamine to pH 10.0 | intensive pink | After the coloring: | +31.74 | +65.82; | −15.24 | white |

What is claimed is:

1. A preparation for dyeing fibers (A), especially human hair, which is prepared by mixing a component and (A1), which contains an enamine, and a component (A2), which contains a carbonyl compound a primary amine, wherein component (A1) has an acidic pH and contains at least one enamine of Formula (I) or its acid addition salt of Formula (Ia)

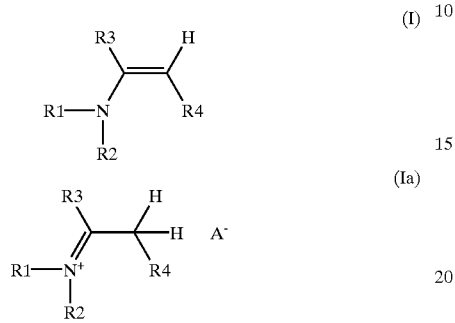

wherein R1 represents a single ring or multi-ring aromatic group, especially an unsubstituted 5-membered or 6-membered aryl group, an unsubstituted 5-membered or 6-membered heterocyclic group, a 5-membered or 6-membered aryl group, substituted with a C1 to C4 alkyl group, a C1 to C4 hydroxyalkyl group, a hydroxy group, a methoxy group, a dialkylamino group or a halogen group, or a 5-membered or 6-membered heterocyclic group, substituted with a C1 to C4 alkyl group, a C1 to C4 hydroxyalkyl group, a hydroxy group, a methoxy group, a dialkylamino group or a halogen group, R2 is a linear or branched C1 to C8 alkyl group, a linear or branched C1 to C8 hydroxyalkyl group or a C1 to C8 alkoxyalkyl group, wherein oxygen atoms may be located between the carbon atoms of the alkyl chain, R3 is a linear or branched C1 to C8 alkyl group, a C1 to C8 alkoxyalkyl group, a linear or branched C1 to C8 alkylene group, a C1 to C8 alkoxyalkylene group, an oxygen atom, a sulfur atom, an —NH group, or an —NR group, wherein R is an alkyl group, an alkoxyalkyl group, a hydroxyalkyl group or hydrogen, the R1 and R3 groups, together with the nitrogen atom and the carbon atom of the basic enamine structure being able to form a cyclic compound and R4 being hydrogen, a linear C1 to C4 alkyl group or a branched C1 to C4 alkyl group, A⁻ being the anion of an organic or inorganic acid, and the component (A2) having an alkaline pH and containing at least one carbonyl compound and at least one primary amine.

2. The preparation of claim 1, wherein the compound of formula (I)/(Ia) is selected from enamines of Formulas (II) to (IX), in which X is a carbon atom, substituted with two C1 to C4 alkyl groups, which may be the same or different, a carbon atom, substituted with a C1 to C4 alkyl group and a hydroxy group, a sulfur atom, an alkylated nitrogen atom, a not-alkylated nitrogen atom or an oxygen atom, and R2 is a linear or branched C1 to C8 alkyl group, a linear or branched C1 to C8 hydroxyalkyl group, or a C1 to C8 alkoxyalkyl group, in which there may be oxygen atoms between the carbon atoms of the alkyl chain, R4 is hydrogen, a linear C1 to C4 alkyl group or a branched C1 to C4 alkyl group, R5, R6, R7 and R8 independently of one another are hydrogen, a linear or branched C1 to C4 alkyl group, a linear or branched C1 to C4 hydroxyalkyl group, a hydroxy group, a methoxy group, an amino group, a monoalkylamino group, a dialkylamino group, a benzyl group or a halogen atom, R9 is hydrogen, a linear C1 to C4 alkyl group or a branched C1 to C4 alkyl group and A⁻ is chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenylborate, formate, acetate or propionate

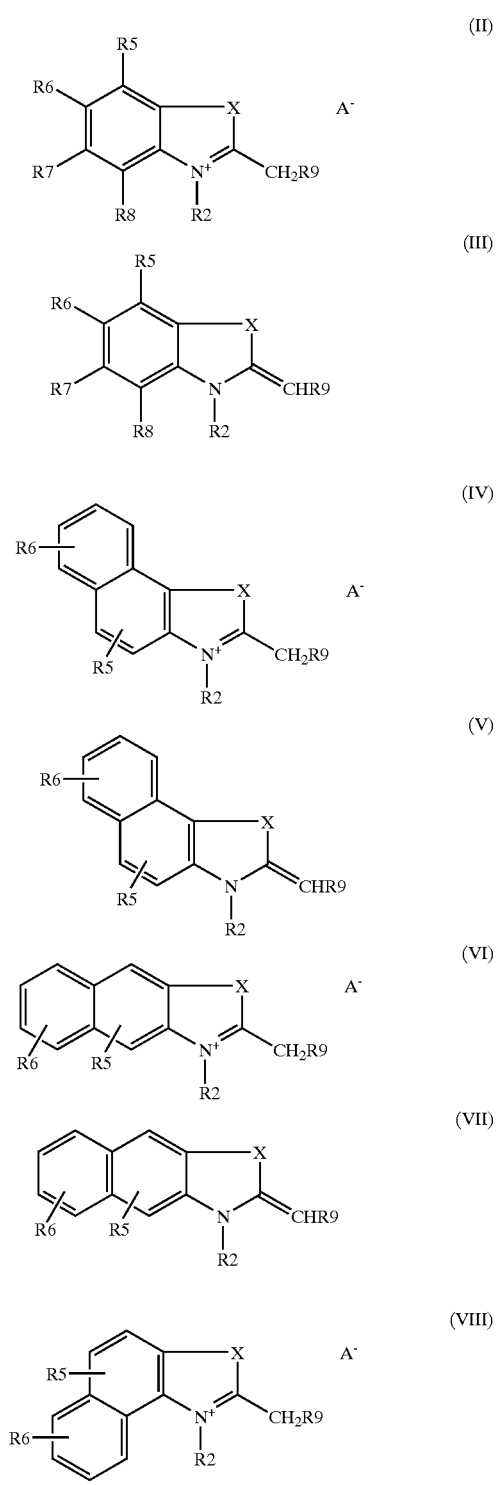

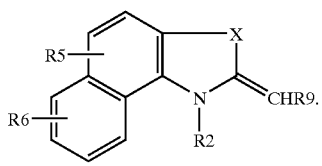

3. The preparation of claim 1, wherein the compound of Formulas (I) to (IX) is selected from 1,3,3-trimethyl-2-methylene-indoline as well as its salts, 1,3,3,4-tetramethyl-2-methylene-indoline as well as its salts, 1,3,3,5-tetramethyl-2-methylene-indoline as well as its salts, 1,3,3,6-tetramethyl-2-methylene-indoline as well as its salts, 1,3,3,7-tetramethyl-2-methylene-indoline as well as its salts, 1,3,3,6,7-pentamethyl-2-methylene-indoline as well as its salts, 1,3,3,5,7-pentamethyl-2-methylene-indoline as well as its salts, 1,3,3,4,7-pentamethyl-2-methylene-indoline as well as its salts, 5-chloro-1,3,3-trimethyl-2-methylene-indoline as well as its salts, 5-fluoro-1,3,3-trimethyl-2-methylene-indoline as well as its salts, 5-isopropyl-1,3,3-trimethyl-2-methylene-indoline as well as its salts, 5-hydroxy-1,3,3-trimethyl-2-methylene-indoline as well as its salts, 5-methoxy-1,3,3-trimethyl-2-methylene-indoline as well as its salts, 5-amino-1,3,3-trimethyl-2-methylene-indoline as well as its salts, 6-hydroxy-1,3,3-trimethyl-2-methylene-indoline as well as its salts, 6-methoxy-1,3,3-trimethyl-2-methylene-indoline as well as its salts, 5-methoxy-6-amino-1,3,3-trimethyl-2-methylene-indoline as well as its salts, 5,6-dihydroxy-1,3,3-trimethyl-2-methylene-indoline as well as its salts, 5,6-dimethoxy-1,3,3-trimethyl-2-methylene-indoline as well as its salts, 4,5,-dihydroxy-1,3,3-trimethyl-2-methylene-indoline as well as its salts, 5,7-dihydroxy-1,3,3-trimethyl-2-methylene-indoline as well as its salts, 5-amino-6-methoxy-1,3,3-trimethyl-2-methylene-indoline as well as its salts, 5-amino-7-hydroxy-1,3,3-trimethyl-2-methylene-indoline as well as its salts, 5-hydroxy-7-amino-1,3,3-trimethyl-2-methylene-indoline as well as its salts, 1-(2'-hydroxyethyl)-3,3-dimethyl-2-methylene-indoline as well as its salts, 1,3,3-trimethyl-2-methylene-3H-benz[e]indole as well as its salts and N-ethyl-2-methylene-benzthiazole as well as its salts.

4. The preparation of claim 1, wherein the carbonyl compound is selected from 4-hydroxy-3-methoxy-benzaldehyde, 3-hydroxy-4-methoxy-benzaldehyde (isovanillin), 3,4-dihydroxybenzaldehyde, 4-hydroxybenzaldehyde, 3,5-dimethoxy-4-hydroxybenzaldehyde, 4-dimethylaminobenzaldehyde, 4-methyl-5-imidazole-carboxaldehyde, 4-dimethylamino-cinnamaldehyde, 4-hydroxy-2-methoxybenzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxy-biphenyl-1-carbaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carbaldehyde, benzene-1,4-dicarbaldehyde, 4-ethoxybenzaldehyde, 2-methyl-1,4-naphthoquinone, 4-carboxybenzaldehyde, 4-hydroxy-3-methoxy cinnamaldehyde, 3,5-dimethoxy-4-hydroxy-cinnamaldehyde, 3-methoxy-4-(1-pyrrolidinyl)-benzaldehyde, 4-diethylamino-3-methoxybenzaldehyde, 1,2-phthaldialdehyde, pyrrole-2-aldehyde, thiophene-2-aldehyde, thiophene-3-aldehyde, chromone-3-carboxaldehyde, 6-methyl-4-oxo-1(4H)-benzopyran-3-carbaldehyde, N-methylpyrrole-2-aldehyde, 5-methylfurfural, 6-hydroxychromen-3-carboxaldehyde, 6-methylindole-3-carboxaldehyde, 4-dibutylamino-benzaldehyde, N-ethylcarbazole-3-aldehyde, 4-diethylamino-2-hydroxybenzaldehyde, 3,4-dimethoxy-5-hydroxybenzaldehyde, 5-(4-(diethylamino)phenyl)-2,4-pentadienal, 2,3-thiophene-dicarboxaldehyde, 2,5-thiophene-dicarboxaldehyde, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

5. The preparation of one of the claim 1, wherein the primary amine is selected from alkanolamines, aromatic amines and amino acids.

6. The preparation of claim 5, wherein the primary amine is selected from monoethanolamine, isopropanolamine, 1-amino-2-propanol, 3-amino-1-propanol and arginine.

7. The preparation of one of the claim 1, wherein the component (A1) has a pH of 1 to 4.5.

8. The preparation of claim 1, wherein the component (A2) has a pH of 7.5 to 12.

9. The preparation of one of the claim 1, wherein the agent contains the compounds of Formulas (I) to (X), the carbonyl compounds and the amines in each case in a total amount of 0.01 to 10% by weight, based on the ready-for-use preparation.

10. A method for temporarily coloring fibers, especially hair, for which the fibers are colored with a preparation of claim 1 and decolorized once again at any later time, wherein a sulfite-containing preparation is allowed to act on the colored fibers for a period of 5 to 60 minutes at a temperature of 20° C. to 50° C. on the colored fibers for the purpose of decolorizing them.

11. A multi-component kit, comprising a component (A1), containing an enamine of Formula (I), and a component (A2), containing a carbonyl compound and a primary amine.

* * * * *